United States Patent
Lemaitre et al.

(10) Patent No.: US 11,464,484 B2
(45) Date of Patent: Oct. 11, 2022

(54) SYSTEMS AND METHODS OF ESTABLISHING A COMMUNICATION SESSION FOR LIVE REVIEW OF ULTRASOUND SCANNING

(71) Applicant: Clarius Mobile Health Corp., Burnaby (CA)

(72) Inventors: Julien Lemaitre, Vancouver (CA); Kris Dickie, Vancouver (CA); Laurent Pelissier, North Vancouver (CA); Trevor Stephen Hansen, North Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 462 days.

(21) Appl. No.: 16/135,617

(22) Filed: Sep. 19, 2018

(65) Prior Publication Data
US 2020/0085408 A1 Mar. 19, 2020

(51) Int. Cl.
*A61B 8/00* (2006.01)
*H04N 7/14* (2006.01)
(Continued)

(52) U.S. Cl.
CPC .......... *A61B 8/4427* (2013.01); *A61B 8/467* (2013.01); *H04L 51/224* (2022.05); *H04L 67/55* (2022.05); *H04N 7/147* (2013.01)

(58) Field of Classification Search
CPC ...... A61B 5/0002; A61B 8/565; H04N 7/147; H04L 12/1818
See application file for complete search history.

(56) References Cited

U.S. PATENT DOCUMENTS 8,297,983 B2 10/2012 Savitsky et al.
9,021,358 B2 4/2015 Amble et al.
(Continued)

FOREIGN PATENT DOCUMENTS

WO 2018081297 A1 5/2018
WO 2018098195 A1 5/2018

OTHER PUBLICATIONS

Applied Radiology, The Journal of Practical Medical Imaging and Management, "Benefits of remote radiologist-mentored emergency tele-ultrasound exams", publication date unknown, available online: https://appliedradiology.com/articles/benefits-of-remote-radiologist-mentored-emergency-tele-ultrasound-exams, last accessed Jun. 28, 2018.
(Continued)

*Primary Examiner* — Amanda Lauritzen Moher
*Assistant Examiner* — Delia M. Appiah Mensah
(74) *Attorney, Agent, or Firm* — Julian Ho; Susan Ben-Oliel (57) ABSTRACT

An application running in a mobile device displays an ultrasound image obtained by a connected ultrasound scanner. A button is displayed on the device, which, when activated, automatically connects the device to a remote reviewer in a virtual videoconferencing room, without the operator of the scanner needing to input user credentials. Upon activating the button, or otherwise triggering the request for a review, pre-stored login credentials are automatically retrieved and used for connecting the operator to the room. The remote reviewer may be connected to the room upon accepting the request for review, without having to input user credentials, which are pre-stored and automatically retrieved.

16 Claims, 5 Drawing Sheets

(51) Int. Cl.
  *H04L 51/224* (2022.01)
  *H04L 67/55* (2022.01)

(56) References Cited

U.S. PATENT DOCUMENTS

| | | |
|---|---|---|
| 2005/0049495 A1 | 3/2005 | Sumanaweera et al. |
| 2011/0015504 A1* | 1/2011 | Yoo .................... G06F 3/0219 |
| | | 600/301 |
| 2011/0306025 A1 | 12/2011 | Sheehan et al. |
| 2013/0296707 A1 | 11/2013 | Anthony et al. |
| 2014/0011173 A1 | 1/2014 | Tepper et al. |
| 2015/0005630 A1 | 1/2015 | Jung et al. |
| 2015/0193586 A1* | 7/2015 | Amble .................. G16H 30/20 |
| | | 705/2 |
| 2017/0105701 A1 | 4/2017 | Pelissier et al. |
| 2017/0325786 A1 | 11/2017 | Pepe |
| 2019/0082144 A1* | 3/2019 | Hakata ............... H04N 5/23238 |

OTHER PUBLICATIONS

Crawford et al., How to set up a low cost tele-ultrasound capable video conderencing system with wide applicability, May 2012, Critical Ultrasound Journal, 4:13.

\* cited by examiner

SYSTEMS AND METHODS OF ESTABLISHING A COMMUNICATION SESSION FOR LIVE REVIEW OF ULTRASOUND SCANNING

TECHNICAL FIELD

This disclosure relates to remotely reviewing ultrasound images. In particular, it relates to systems and methods of establishing a communication session for live review of ultrasound scanning.

BACKGROUND

Ultrasound is a useful, non-invasive imaging technique capable of producing real time images. Ultrasound imaging has an advantage over X-ray imaging in that ultrasound imaging does not involve ionizing radiation.

It can be difficult to properly capture and analyse ultrasound images. The successful use of ultrasound is dependent on highly-skilled technicians to perform the scans and experienced physicians to interpret them. It typically takes several years of training for a technician to become proficient.

Trained ultrasound technicians are not universally accessible. Ultrasound could be used to improve care for more patients, especially in rural and low-resource settings, if less-skilled operators were able to perform ultrasound examinations quickly and accurately.

Traditional real-time tele-sonography systems typically rely on conventional multimedia communications to enable two-way communication between the examiner and a remote expert. The ultrasound imaging data can be streamed in real-time and displayed simultaneously with a video stream that provides a view of the ultrasound image. In some cases, this display of the video stream is also shown with a real-time video stream depicting the patient and the probe. A remote expert can provide live voice instructions and certain other feedback to the operator.

Ultrasound systems are not typically provided with videoconferencing technology, so third-party platforms are used to provide the underlying audio and video infrastructure. When performing tele-ultrasound using traditional systems, the operator is required to login to a video conferencing system in the middle of the ultrasound scanning examination. This process is cumbersome, and interrupts the workflow of the ultrasound operator. The need to login to a video conferencing system may also discourage some ultrasound operators from using tele-ultrasound, because they would need to recall and enter user credentials to establish a live connection to a remote reviewer.

There is thus a need for improved systems and methods of establishing a communication session for live review of ultrasound scanning. The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

The present invention may generally allow for connection of an ultrasound operator to a remote ultrasound reviewer in real time, during an ultrasound examination, without the need for the operator to enter login credentials to a video conferencing system. Configuration data for connecting the operator to a virtual videoconferencing room may be stored beforehand in the system. The system, upon receiving a request to connect to a reviewer, may automatically retrieve the data and use it to make the connection to the room. Likewise, the reviewer may be automatically connected to the room using stored login credentials.

Various embodiment of the invention may or may not provide one or more of the benefits of: being more convenient for an ultrasound operator to use; being easier for an ultrasound operator to use; presenting fewer hurdles for an ultrasound operator to use; being more convenient for an ultrasound reviewer to use; increasing the efficiency in which ultrasound examinations are reviewed; and/or reducing the costs associated with reviewing ultrasound examinations.

A. Glossary

Operator—the person that operating an ultrasound scanner (e.g., a clinician, medical personnel, a sonographer, ultrasound student, ultrasonographer and/or ultrasound technician).

Reviewer—the person who looks at and/or interprets the ultrasound images remotely from the location where the images are captured. The reviewer may be a radiologist, physician, ultrasound educator and/or other personnel familiar with medical diagnostic ultrasound imaging. By "remotely", it is meant that the reviewer and operator are in different rooms in the same building, in different buildings, in different cities and/or in different countries.

The term "module" can refer to any component in this invention and to any or all of the features of the invention without limitation. A module may be a software, firmware or hardware module, and may be located in a user device or a server.

The term "network" can include both a mobile network and data network without limiting the term's meaning, and includes the use of wireless (e.g. 2G, 3G, 4G, 5G, Wi-Fi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A network could also mean dedicated connections between computing devices and electronic components, such as buses for intra-chip communications.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by code or a module. The processor, if comprised of multiple processors, may be located together or geographically separate from each other. The term includes virtual processors and machine instances as in cloud computing or local virtualization, which are ultimately grounded in physical processors.

The term "system" when used herein, and not otherwise qualified, refers to a system for automatically establishing a communications link between an operator and a reviewer, the system being the subject of the present invention.

The term "ultrasound image" herein refers to a live video ultrasound image. A frame of the ultrasound image is referred to as a "still".

The term "user" refers to a person who uses the system or interacts with it via a user device. There may be different types of user, such as an operator and a reviewer.

B. Exemplary Embodiments

Figure 1:
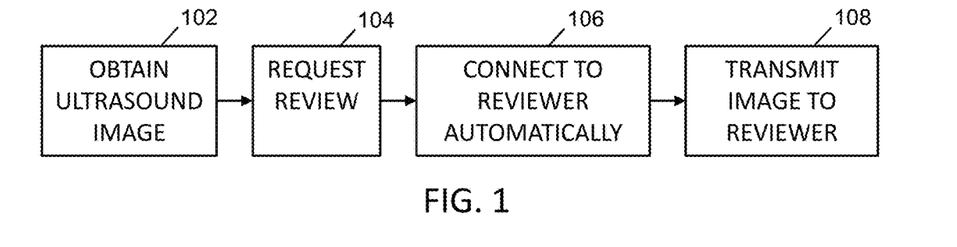
FIG. 1 is a flowchart of the main steps of a method for automatically connecting an operator to a reviewer during an ultrasound examination, in accordance with at least one embodiment of the present invention.

Referring to FIG. 1, a flowchart summarizes the main steps undertaken in an exemplary embodiment of the invention. In step 102, an operator of an ultrasonic scanner (or scanner, ultrasonic transducer or ultrasonic probe) obtains an ultrasound image of a subject, which is displayed on a mobile device of the operator. In step 104, the operator requests, using the mobile device, a real-time review of the ultrasound image, which is to be understood as a real-time video stream of ultrasound images. In step 106, in response to the request for a review, the system automatically connects the operator to a reviewer, by establishing a two-way communication link between the mobile device of the operator and a computing device of the reviewer. Once the communication link has been established, the ultrasound image is transmitted, in step 108, to the reviewer's computing device, and the reviewer and operator are able to communicate with each other in real-time via the established link, to discuss the image.

Figure 2:
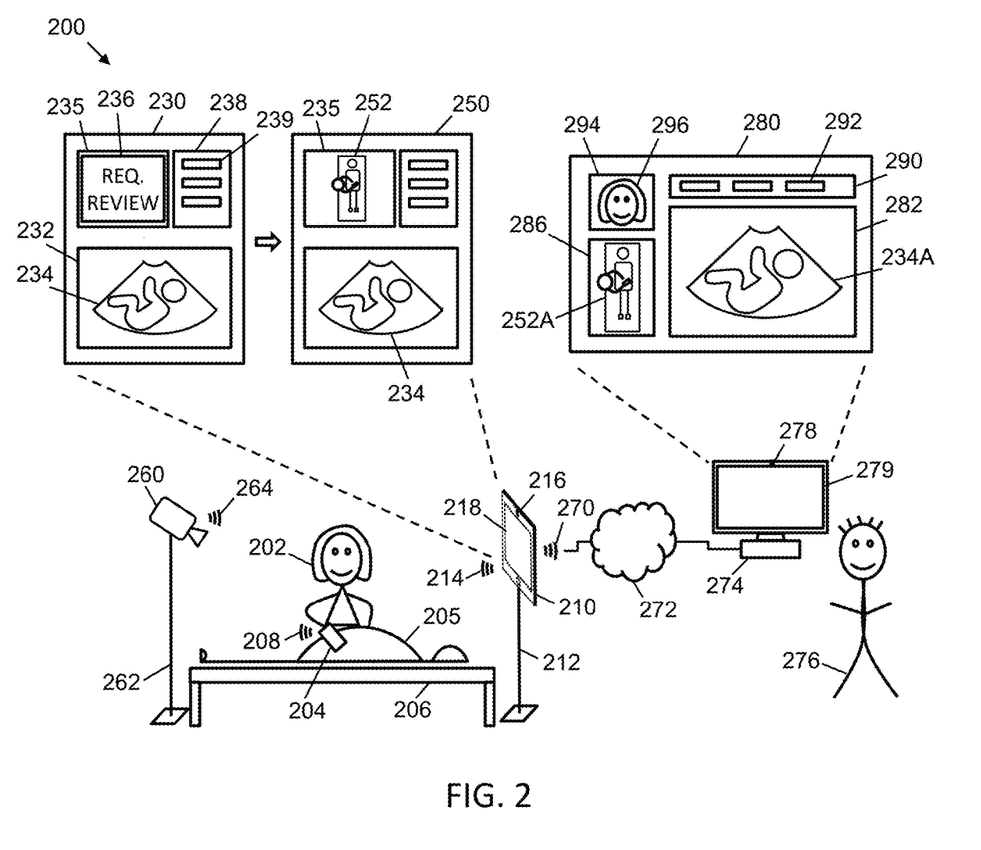
FIG. 2 is a schematic diagram (not to scale) of a system for automatically connecting an operator to a reviewer during an ultrasound examination, in accordance with at least one embodiment of the present invention.

Referring to FIG. 2, an exemplary embodiment is shown of the system 200 for automatically connecting an operator to a reviewer during an ultrasound examination. An operator 202 is holding a scanner 204 that she is using to examine a subject 205 lying on the bed 206. While illustrated as a human patient in FIG. 2, the present embodiments may be practiced while the ultrasound operator is scanning any subject (e.g., a human or veterinarian patient, a phantom, and/or any other person or object that is being scanned). In the illustrated example, the scanner 204 has a wireless communications connection 208 via which it communicates with the mobile device 210 of the operator 202. The mobile device 210 is a smart phone or a tablet, for example, mounted on a stand 212. The mobile device 210 communicates with its wireless connection 214 to the scanner 204. The wireless connection (208, 214) between the scanner 204 and the mobile device 210 may operate using a Wi-Fi™ protocol, as this type of protocol can provide enough bandwidth for communicating high resolution ultrasound images.

The mobile device 210 is shown on the stand 212 for convenience, but in other embodiments, it can be held by hand by the operator 202. In the embodiment shown, a camera 216 of the mobile device 210 is directed so as to capture an image of the subject 205 and the location and orientation of the scanner 204 on the subject 205. The position of the mobile device 210 may be different from that shown here, and may be at the foot or side of the bed 206, or held by the other hand of the operator 202, for example. In embodiments where the mobile device 210 is held by hand, the rear-facing camera can be used to capture the image of the subject 205.

Displayed on the screen 218 of the mobile device 210 is a screen shot 230, which includes a first display area 232 with a real-time ultrasound image 234. The image 234 is being transmitted from the scanner 204 to the mobile device 210 in real time. As used herein, the term "real time" refers to live, synchronous communications that can occur without transmission delays and with minimal latency. A second display area 235 in the screen shot 230 of the mobile device 210 may be a soft button 236 for requesting a review of the ultrasound image 234. A third display area 238 in the screen shot 230 may be a menu with various menu items 239, for example, for controlling the scanner 204, for adjusting the image 234 and for saving stills of the image 234. In other embodiments, the button 236 is one of the menu items 239.

When the review request button 236 is tapped by the operator 202, a two-way communications link may automatically be established with a reviewer, and the display of the mobile device 210 may change to the view shown in screen shot 250. In this screen shot 250, the first display area 235 switches to display an image 252 of the subject 205 captured by the front-facing camera 216 of the mobile device 210. The image 252 may be adjusted by the operator for convenience of view, e.g., by zooming in or rotating it. Additionally or alternatively, the image 252 may be automatically adjusted. Both the image 252 of the subject 205, showing the location of the scanner 204, and the ultrasound image 234 may be displayed simultaneously on the mobile device 210. Both the image 252 of the subject 205 and the ultrasound image 234 may be transmitted for review by the reviewer 276.

In the present embodiments, all that the operator 202 may need to do to initiate a call with the reviewer 276 is to tap on the button 236. It is configured so that a single tap only on the button 236 is required, e.g., it is a one-click connection. The operator 202 may not need to know which reviewer she is contacting, as the system 200 makes a connection automatically depending on which reviewers are available. In response to tapping on the button 236, e.g., requesting a connection, the connection may be made automatically by the system 200. Additionally or alternatively, the initiation of the call from the operator 202 to the reviewer 276 may be made via a voice command, or it may be automatically initiated by the mobile device 210 upon the detection, by the mobile device 210, that an ultrasound image is being captured. In some embodiments, the ability to activate the button 236 is withheld until an ultrasound image is obtained, or until an ultrasound image has been obtained for a minimum, threshold period of time. This can be indicated to the operator by, for example, graying out the button 236 until it can be activated.

Optionally, a supplementary camera 260 on stand 262 may be used by the operator 202 to capture the image 252 of the subject 205. With this option, the position of the mobile device 210 is not restricted by the need to capture an image of the subject 205. The supplementary camera 260 may be wirelessly connected 264 to the mobile device 210, in order to transmit a captured video stream of the subject 205 to the mobile device 210. The mobile device 210 may then display the captured image from the supplementary camera 260 in the second screen area 235.

The mobile device 210 may be wirelessly connected 270, e.g., via a cellular connection such as an LTE (Long-Term Evolution) connection and/or a Wi-Fi™ connection, and via the internet 272 to a computing device 274, such as a laptop or a desktop computer, that is used by the reviewer 276. For example, in embodiments where the primary Wi-Fi™ connection of the mobile device 210 is used to for communication with a wireless ultrasound scanner 204, it may be desirable to use a cellular connection of the device 210 to form the communication session with the computing device 274. However, in embodiments where the connection between the scanner 204 and the mobile device 210 is formed using a cord or a wireless protocol other than Wi-Fi™, Wi-Fi™ may be used to form the live connection with the computing device 274 of the reviewer 276.

The reviewer computing device 274 optionally has a camera 278 that is directed at the reviewer 276. After a communication link has been established at the request of the operator 202, a screen 279 of the reviewer's computing device 274 may display an example screen shot 280. The screen shot 280 may have a first display area 282, which has an image 234A of the ultrasound scan that is being captured by the scanner 204 and transmitted from the operator's mobile device 210. A second display area 286 may have an image 252A of the subject 205 as captured by the camera 216 (or supplementary camera 260) and transmitted from the operator's mobile device 210. A third screen area 290 may be a menu bar with various menu options 292 for controlling the communication with the operator and for adjusting the images 234A, 252A (e.g. rotating them, changing the brightness, changing the contrast, magnifying them, and/or saving stills of them). A fourth, optional screen area 294 may show an image 296 of the operator 202 in an embodiment where the supplementary camera 260 is being used to capture an image of the subject 205, and the front-facing camera 216 is capturing an image of the operator 202.

While the operator 202 and reviewer 276 are connected in a tele-ultrasound session, the reviewer 276 can provide guidance to the operator 202, for example, by directing the operator 202 as to where to position the scanner 204.

Figure 3:
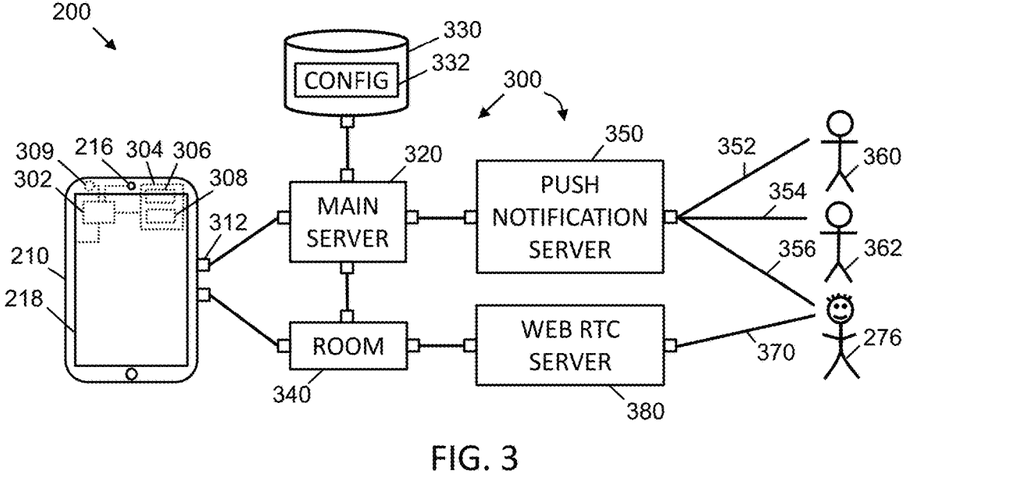
FIG. 3 is a block diagram showing components of the system, in accordance with at least one embodiment of the present invention.

Referring to FIG. 3, further components of the system 200 are shown, which include a group of servers 300. The system 200 may include or interact with the operator's mobile device 210, or any other electronic device that provides the necessary equivalent functionality to fulfill the requirements of the present embodiments. The mobile device 210 may include a processor 302 which is operably connected to computer readable memory 304 included in the mobile device 210. The mobile device 210 may include computer readable instructions 306 (e.g. an application, or app) stored in the memory 304 and computer readable data 308, also stored in the memory 304. The front-facing camera 216 and the rear-facing camera 309 may also be connected to the processor 302. The memory 304 may be divided into one or more constituent memories, of the same or different types. The mobile device 210 may include a display screen 218, also operably connected to the processor 302. The display screen 218 may be a traditional screen, a touch screen, a projector, an electronic ink display and/or any other technological device for displaying information. Mobile device 210 may include multiple physical or virtual ports 312 via which wired or wireless connections are made to ports of other components of the system 200.

The mobile device 210 may be connected via port 312 to a main server 320. The main server 320 may in turn be connected to, or include, database 330, which stores configuration data 332 for the system 200. The main server 320 may also be connected to virtual videoconferencing room 340, in which an ultrasound operator and an ultrasound reviewer may meet to review/discuss an ultrasound examination in real time. The main server 320 may also be connected to a push notification server 350, which can send notifications 352, 354, 356 to available reviewers 360, 362, 276 respectively. The notifications 352, 354, 356 may inform the reviewers 360, 362, 276 that an operator of an ultrasound scanner 204 has requested a review of an ultrasound examination. In this particular scenario, reviewer 276 is responsive and communicates on connection 370 with a web RTC (real-time communications) server 380. The web RTC server 380 may connect the responding reviewer 276 to the virtual room 340. The virtual room 340 may either be provided by the web RTC server 380 or it can be provided by a further server. FIG. 3 highlights the data flows upon the sending of a notification to available reviewers, and upon the connection of the reviewer to the room 340. However, in various embodiments, there may be additional connections amongst the servers shown in FIG. 3 that are not illustrated. For example, in some embodiments, the main server 320 may also be communicably connected to the Web RTC server 380, so as to allow the main server 320 to configure settings thereon.

Each server 320, 350, 380 may include one or more processors that are operably connected to computer readable memory in the server. Each server 320, 350, 380 may include computer readable instructions (e.g. an application) stored in its memory and computer readable data, also stored in its memory. The respective memories may each be divided into one or more constituent memories, of the same or different types. The server applications, when executed by the processor(s) in the servers, provide at least some of the functionality required to automatically connect an ultrasound operator to an ultrasound reviewer.

The configuration data 332 may include, for example, details of the institution (e.g. a hospital, clinic) in which the ultrasound examination is taking place, a virtual room identifier, details of the operator of the ultrasound scanner, and/or details of the reviewers. Details may include, for example, institution identifier, user identifier, and user name and login credentials for each of the operators and the reviewers. The configuration data 332 may be provided to the app 306 in the mobile device 210 upon the app 306 requesting a review or upon the app's initialization, or it is otherwise made available to the other components of the system 200 when and however required to make an automatic connection between an operator and reviewer. The minimum requirement of the configuration data 332 is to include and provide sufficient information for the operator to enter the virtual room 340 in response to a trigger, without the operator needing to input user credentials. The trigger may be, for example, a tap on the review request button 236. In some embodiments, the configuration data is also sufficient for the reviewer to enter the room 340 upon responding affirmatively to a notification that a review is being requested, without the reviewer needing to input user credentials. As such, the storage and timely distribution of the configuration data 332 may allow the system 200 to automatically establish a communication session between an operator and a reviewer upon a request from an operator or some other trigger.

For example, the main server 320 may send the configuration data 332 to the push notification server 350, which may then push it to the computing devices 274 (not shown in FIG. 3) of the reviewers 360, 362, 276 when a call is initiated. One of the reviewers 276 may then answer the call of the operator, and the computing device 274 of the responding reviewer 276 may connect to the video conferencing room 340 using the configuration data 332. Neither the operator 202 nor the reviewer 276 may need to deal with user credentials and logging in, as these aspects are automatically dealt with by the system 200.

In some embodiments, the configuration data 332 may simply contain a virtual room identifier and a network location of the virtual room that allows for entrance into the virtual room 340 (without including details of the operator 202 or the reviewers). This may facilitate ease of providing configuration data 332 in some instances because the same login credentials for the room 340 can be provided to the operator device 210 and all the reviewer devices, without having to customize the notifications to include operator or reviewer identifiers. This is possible because the present embodiments use a virtual room 340 to form a tele-ultrasound session, so that the login credentials for the room 340 can be distributed to each device without either the operator device 210 or any reviewer device needing to know the connection information for the other party. This is unlike traditional tele-ultrasound systems that typically form a direct communication session between an operator device 210 and a reviewer device 274 where at least one of the two devices would need to know some sort of identifier for the other party (e.g., a username or Internet Protocol (IP) address of the other party) to establish the tele-ultrasound session.

Figure 4:
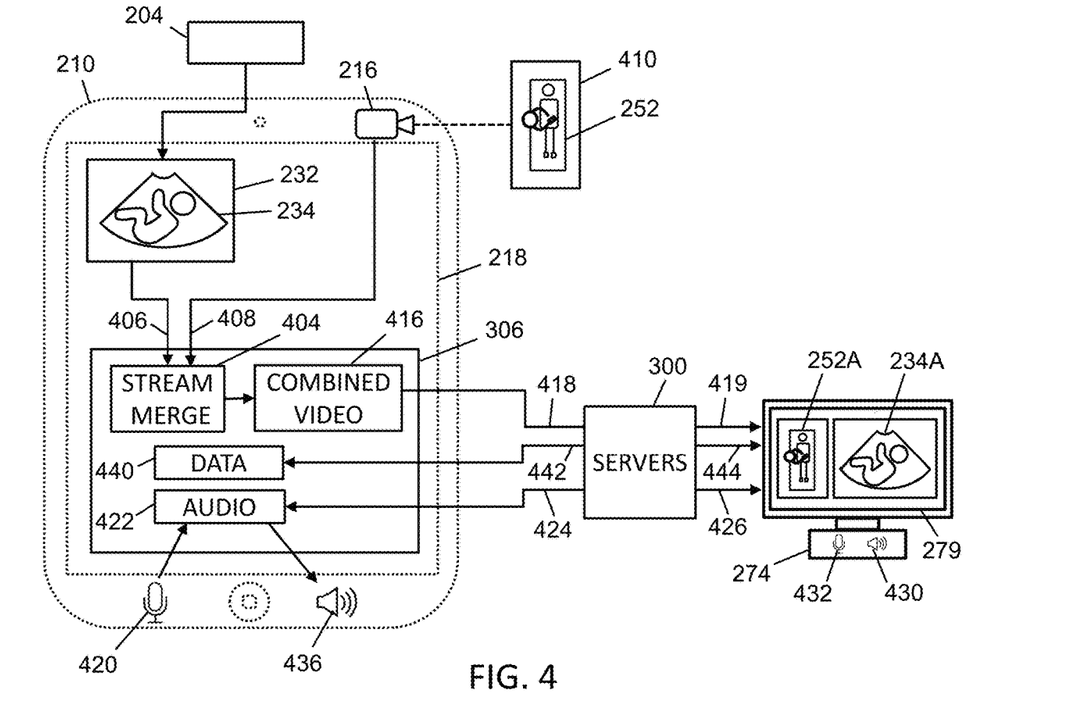
FIG. 4 is a schematic diagram showing modules of the application running on the operator's device, in accordance with at least one embodiment of the present invention.

Referring to FIG. 4, a schematic diagram shows modules of the application 306 running on an operator's mobile device 210. The stream merge module 404 has two inputs 406, 408. Input 406 is the video stream from the scanner 204, which may also provide image 234 of the ultrasound scan on display area 232 of the mobile device's screen 218. The input 408 may be produced by the front-facing camera 216, which captures in its field of view 410 an image 252 of the subject 205. The two inputs 406, 408 may be merged by the stream merge module 404 to result in a combined video stream 416. The combined video stream 416 may then be transmitted on one-way video link 418 to the servers 300.

While FIG. 4 illustrates the inputs 406, 408 being combined prior to transmission, in various embodiments, the two input streams 406, 408 may be transmitted from the mobile device 210 in an uncombined manner (e.g., separate streams for each input 406, 408). Additionally or alternatively, the video streams 406, 408 can be aggregated to be sent via data link 418 without merging them. For example, this may allow the two video streams to remain distinct and/or separable upon their arrival at the computing device 274 of the reviewer 276, while still providing some benefit of combined communication of the two streams 406, 408 to the servers 300. Providing a mechanism that allows each of the streams 406, 408 to be separable and individually identifiable at the computing device 274 may allow the display of the different video streams 406, 408 to be configurable (e.g., repositioned, resized) at the reviewing computing device 274.

The servers 300 may transmit the combined video stream 416 on a one-way video link 419 to the computing device 274 of the reviewer, in which the combined video stream is separated into its constituent parts. As a result, the computing device 274 displays the ultrasound image 234A captured by the scanner 204 and the image 252A of the subject 205 in separate areas of the display screen 279.

The microphone 420 of the mobile device 210 may capture audio signals and the audio module 422 of the app 306 may transmit them via two-way audio link 424, 426 to the reviewer's computing device 274, where they are output on speaker 430. Audio from the reviewer 276 may then be captured by the microphone 432 on the reviewer's computing device 274 and transmitted to the audio module 422 of the app 306 on two-way audio connection 426, 424. Audio signals received from the reviewer 276 may then be output on the speaker 436 of the mobile device 210.

In some embodiments, the data module 440 may receive data from the reviewer's computer 274 along data links 442, 444. The data may include screen coordinates of, for example, a point of interest on the ultrasound image that the reviewer has marked with a cursor, and that the operator should investigate more closely. Additionally or alternatively, the data may be assets (e.g., pre-recorded videos) that may show certain scanning techniques. For example, such assets may be useful if the present embodiments are used in educational settings, as discussed in greater detail below. Additional examples of data that may be transmitted from a reviewer's computer 274 include one or more of: different types of videos or graphics (e.g., in compressed form, or as a file provided in the Graphics Interchange Format (GIF)); still images; documents for applicable literature (e.g., that may be useful for a student learning ultrasound or a particular medical specialty—as may be provided in Microsoft Office™ formats or Portable Document Format (PDF)); and/or labels or annotations linked to cursor points (e.g., to suggest or identify landmarks/structures at a cursor position). In various embodiments, the data that can be transmitted from the reviewer's computer 274 may also be called assets.

In various embodiments, the same or a different data module 440 may be configured to transmit data to the computing device 274 of the reviewer (e.g., along data links 442, 444). For example, this data may include contextual information about the scanning being performed. In an example scenario where there is live scanning of a patient, the data transmitted to the computing device 274 may include patient information (e.g., medical history, medication, drug allergies, or the like), and/or information about the intake condition of the patient (e.g., if the patient was subject to trauma).

Figure 5:
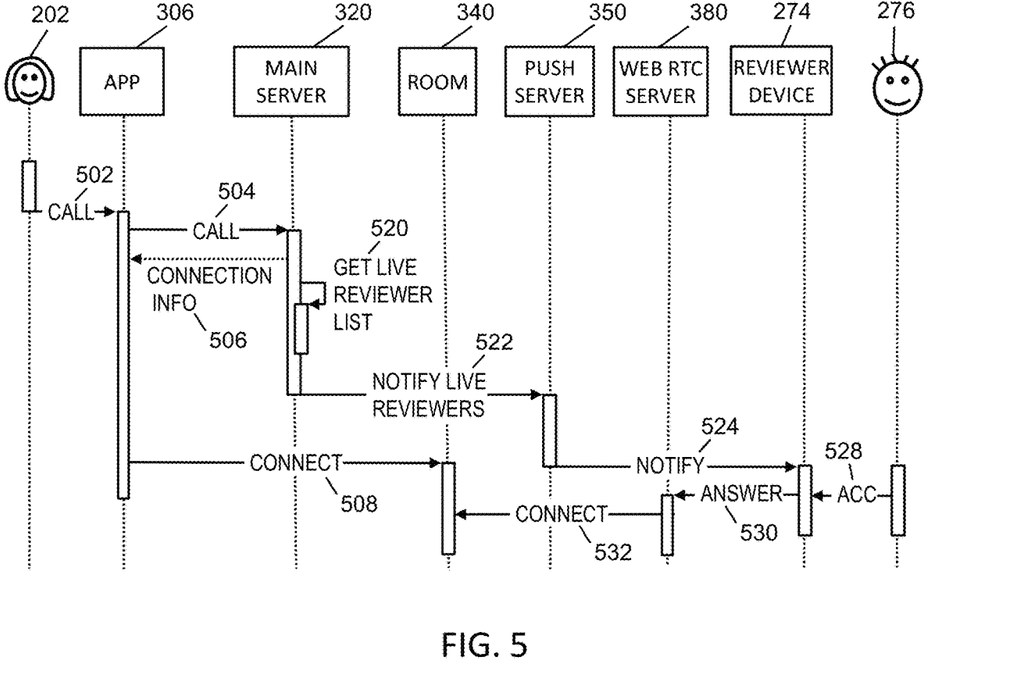
FIG. 5 is a sequence diagram of a method for automatically connecting an operator to a reviewer during an ultrasound examination, in accordance with at least one embodiment of the present invention.

Referring to FIG. 5, a sequence diagram is shown for automatically connecting an operator 202 to a reviewer 276 during an ultrasound examination. In discussing FIG. 5, reference will also be made to the elements of the earlier figures. At step 502, the operator 202 may call for a live review by, for example, tapping a button 236 that is displayed on the screen 218 of the mobile device 210 on the app 306 running on the mobile device 210. In response to this, at step 504, the app 306 may transfer the call to the main server 320, which responds back to the app 306 with the connection information 506 that may be used by the app 306 to automatically connect into the virtual videoconferencing room 340, without the operator 202 needing to take any further steps. Upon receipt of the connection information 506, the app 306 may connect, at step 508, to the room 340. As the app 306 is connecting to a room 340 rather than a specific reviewer, it may not be necessary for the operator 202 to know which reviewer is to be called.

Meanwhile, in response to receiving the call 504 from the app 306 on the operator's mobile device 210, the main server 320 may retrieve a live reviewer list at step 520, as well as all the necessary configuration data from the database 330. In some embodiments, the live reviewer list may be derived from a timetable of reviewer availabilities, and/or other schedule (e.g., an on-call schedule for physicians). There may be several reviewers who are subscribed to the system 200, but they may not all necessarily be available at a specific time, such as when the operator 202 initiates a call 502. Additionally or alternatively, the reviewer list may be determined based upon a particular medical specialty (e.g., of the operator 202).

In various embodiments, the list of live reviewers may be ultrasound experts within the same institution that the operator 202 belongs to. For example, in a system where use of ultrasound scanners 204 are administered by an online administration portal that can limit access to the scanners 204 via limiting use of the app 306, the online portal may be configured to allow adding of certain users within an institution to be on the live reviewer list.

Using the obtained list, the main server 320 may request, at step 522, the push server 350 to notify the reviewers that are currently available. In response to the request from the main server 320, the push server 350 may then notify the computing devices 274 (e.g. a desktop computer or another mobile device) associated with the available reviewers at step 524. Notifications may be sent via a text message or email, for example, or via a pop-up message that appears on the reviewer's computing device 274. Notifications may be sent to other of the reviewer's devices 274 (if a reviewer has more than one device 274), or multiple of the reviewer's devices 274.

The reviewer 276 that accepts (ACC) the request to review, at step 528, is then connected to the web RTC server 380 in step 530, from the reviewer's computing device 274. The action required from the reviewer 276 to join the room can be, for example, a tap on an "Accept" link that is transmitted in the notification. The information needed to connect the reviewer 276 to the room may be contained in the link, having been transferred from the main server 320 and the push server 350 in turn.

In other embodiments, the information needed to connect to the room is stored in the reviewer's computer 274. Additionally or alternatively, this information may be provided via notification platforms. For example, the information may be embedded in a notification of a wearable device (e.g., a smartwatch such as the Apple Watch™), smart glasses, augmented reality (AR) goggles, and/or other device. In the example where the notification is provided in the notification platform of smart glasses or AR goggles, the notification may be configured to automatically bring up the video streams on a viewport and/or automatically enter a virtual reality (VR) or AR room with the operator 202.

In further embodiments, a reviewer 276 may use a reviewing device 274 to log into a portal showing available rooms 340, so as to select a room and manually log in. Such a configuration may be desirable in an educational setting where the tele-ultrasound session was scheduled in advance.

At step 532, the web RTC server 380 may connect the reviewer's computing device 274 to the room 340. Upon both the app 306 and the reviewer device 274 connecting to the room 340, two-way communication between the operator 202 and the reviewer 276 can commence, with the reviewer 276 being able to see the ultrasound image.

In various embodiments, the room 340 may be joined by multiple reviewers (e.g., to allow for a collaborative consultation with additional reviewers in other specialties). This may be implemented by allowing the notifications sent at act 524 to remain active so as that a secondary reviewer (e.g., reviewers 360, 362 shown in FIG. 3) may also join the room 340. Additionally or alternatively, the system may be configured to restrict the tele-ultrasound session to a single reviewer 276. In this case, the available reviewers that did not respond to the notification in the affirmative may be notified that the request for review has been taken up by another reviewer.

In various embodiments, the operator 202 can call the reviewer 276 at any time, either before starting to scan, during the scan or after the scan.

Figure 6:
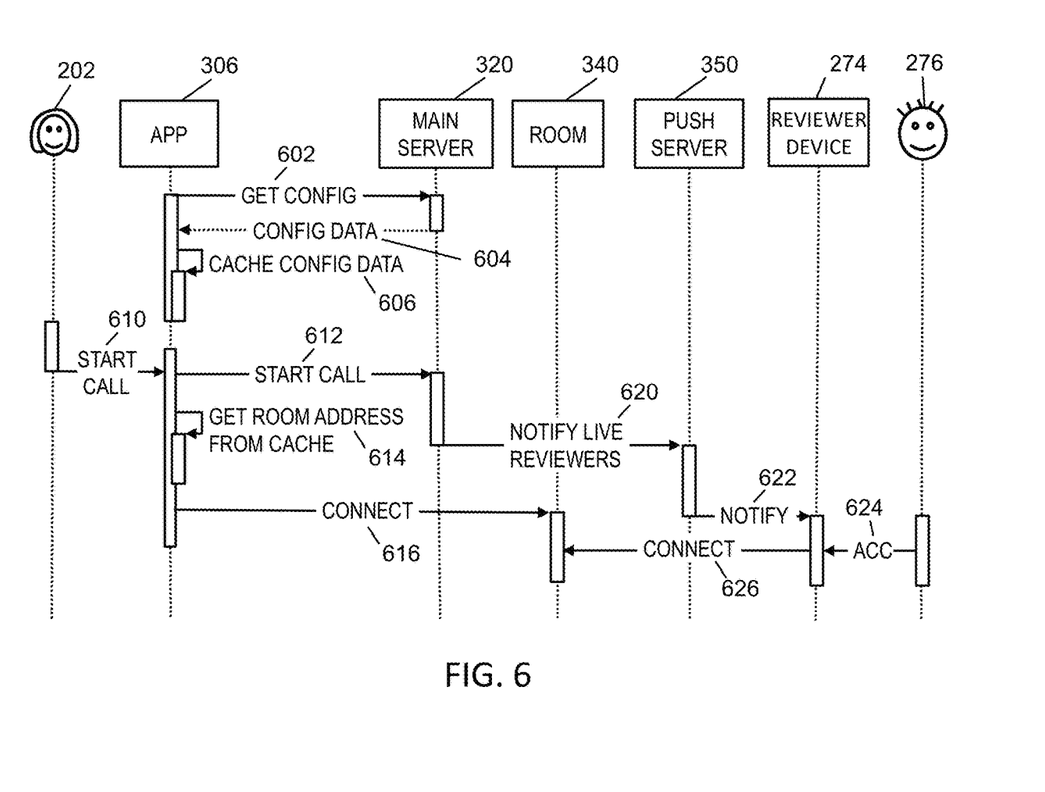
FIG. 6 is a sequence diagram of an alternate method for automatically connecting an operator to a reviewer during an ultrasound examination, in accordance with at least one embodiment of the present invention.

Referring to FIG. 6, an alternate method for automatically connecting an operator 202 to a reviewer 276 is shown. In discussing FIG. 6, reference will also be made to the elements of the earlier figures. During initialization of the app 306, the app 306 may retrieve the configuration data 332 from the main server 320 at steps 602 and 604. At step 606, the app 306 may cache the configuration data 332 for future use. In some embodiments, the app 306 may not be initialized, and will be prevented from connecting to a reviewer unless the configuration data is retrieved and cached by the app 306.

After the app 306 has been initialized, the app 306 may be used to perform an ultrasound examination. During an ultrasound examination, the operator 202 may initiate a call using the app 306 at step 610. In response, at step 612, the app 306 may transmit the request to start a call to the main server 320. Using the configuration data obtained from the cache (step 614), the app 306 may automatically connect to the room 340 (step 616).

Meanwhile, using the configuration data 332 from the cache, the main server 320 may request, at step 620, the push server 350 to notify the reviewers that are currently available. In response to the request from the main server 320, the push server 350 may then notify the available reviewers at step 622 by sending a notification to their computing devices. The reviewer 276 that responds at step 624 to the notification in order to accept the request for review may then be connected by the reviewer's computing device 274 to the room 340 (act 626).

C. Variations

Variations of the embodiments described herein are possible.

For example, as discussed above in relation to FIG. 2, the supplementary camera 260 may generally be providing images to the operator's device 210. However, in an alternative embodiment, the supplementary camera 260 may not connect to the operator's device 210. Instead, the supplementary camera 260 may be connected to the room 340 via a separate computer. This embodiment is shown generally as 700 in FIG. 7.

Figure 7:
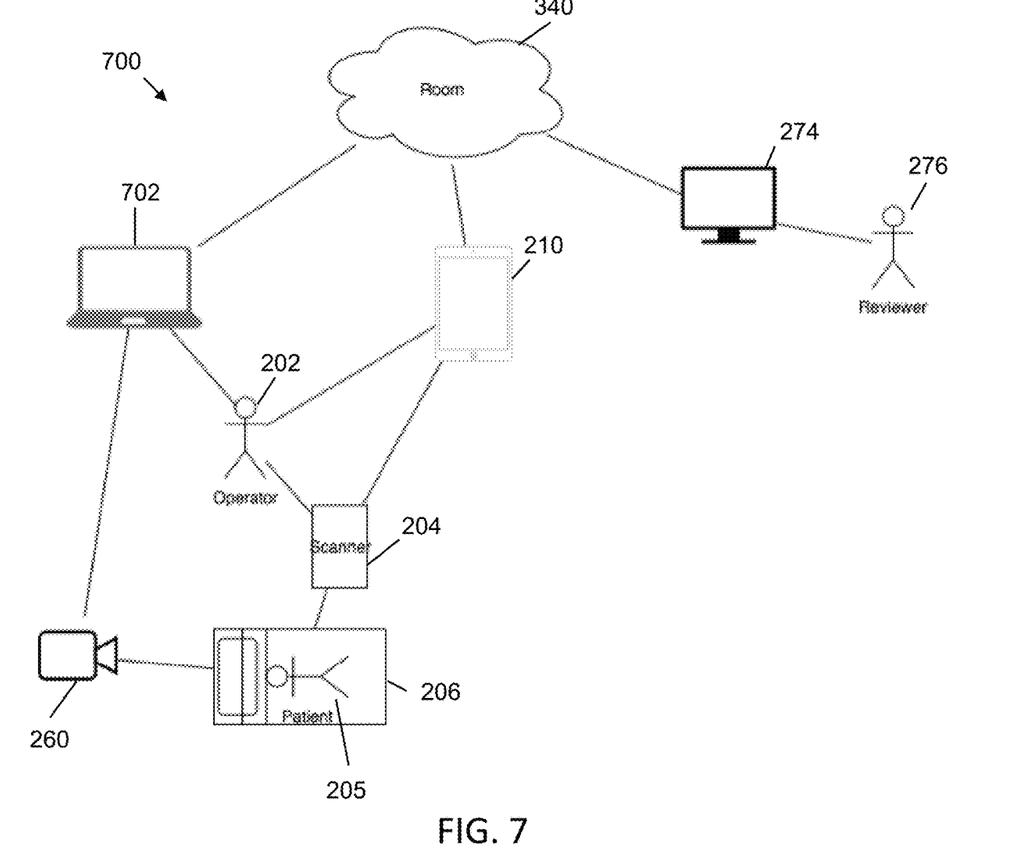
FIG. 7 is a schematic diagram of a system for automatically connecting an operator to a reviewer during an ultrasound examination, in accordance with at least another embodiment of the present invention.

In FIG. 7, an ultrasound scanning session may be performed by operator 202 using scanner 204 on a subject 205 (e.g., a patient on bed 206). The ultrasound images may be viewed on mobile device 210, and as discussed above, a tele-ultrasound session may be established using virtual room 340 between the mobile device 210 and the computing device 274 of the reviewer 276. As shown in FIG. 7, a supplemental camera 260 may also be provided. However, instead of the supplemental camera 260 connecting to the mobile device 210 for transmission to the virtual room 340 (as was discussed above in relation to FIG. 2), the supplemental camera 260 may be communicably connected to a separate computing device 702 that can independently join the virtual room 340 to participate in the tele-ultrasound session with the operator and the reviewer 276. As shown in the example illustration of FIG. 7, the operator 202 is operating this computing device 702. However, other configurations may be possible. Also, the computing device 702 is shown as a laptop, but any other computing device suitable of establishing a connection with the supplemental camera 260 may be possible. Such a configuration may reduce computation load and/or bandwidth constraints on the operator's primary mobile device 210 (which may already need to process and transmit two video streams from the scanner 204 and its own camera).

Further variations are possible. For example, in some embodiments, the operator's device 210 may be a laptop computer. Additionally or alternatively, other wireless communication protocols may be used provided that they can support sufficient bandwidth for transmitting the video streams. Additionally or alternatively, a different number or configuration of servers may be used in other embodiments to achieve the same result as described above. For example, the functions of the servers 300 (as shown in FIG. 3) may be embodied in a single server. A single server can be interpreted as including multiple constituent servers. Additionally or alternatively, the video links 418, 419 (as shown in FIG. 4) may be two-way video links in embodiments where the video image of the reviewer 276 is transmitted back to the operator 202.

In embodiments where the mobile device 210 is held in one hand by the operator 202 and the scanner 204 is held in the operator's other hand, the location of the button 236 (as shown in FIG. 2) may be such that it can be activated by a thumb of the hand that is holding the mobile device 210. For example, for physically-larger mobile devices 210, the button 236 may be located on the left side of the screen 218 when the mobile device 210 is held in the operator's left hand.

In some embodiments, the button 236 for activating a tele-ultrasound session may be configured to be visible in a single location (e.g., top or bottom of screen) at all times, so as to have access to tele-ultrasound assistance on any screen/page that the app 306 is currently showing regardless of whether live scanning is occurring. For example, this button 236 may be shown on screens of the app 306 that are typically configured for entry of patient information, review of already-saved ultrasound images, or the like.

Additionally or alternatively, mechanisms other than the button 236 may be used to activate a tele-ultrasound session. For example, these mechanisms may include using voice control (e.g., using voice assistants such as Apple™ Siri™, Google Assistant™ and/or Amazon™ Alexa™) and/or receiving input via a button on the scanner 204. In further embodiments, artificial intelligence (AI) may be used to determine when a tele-ultrasound session should be activated. For example, AI with pre-trained models on potentially-suspicious structures may be used to continuously assess the images being obtained. If this continuous assessment results in a match with the suspicious structures, this may trigger the app 306 to activate a tele-ultrasound session.

In various embodiments, the system may be configured to manage multiple concurrent communications between multiple operators and multiple reviewers, using multiple virtual rooms.

In the embodiments where the operator's device 210 is handheld, the rear-facing camera may be used to capture an image of the subject and the position of the scanner 204 on the subject 205. In this case, the front-facing camera of the operator's device 210 may additionally or alternatively be used to capture a video of the operator 202, which may then be transmitted to the virtual room 340, provided that the rear-facing and forward-facing cameras can be operated simultaneously.

In various embodiments, one or more of the web RTC server 380, the push notification server 350, and/or database 330 (as shown in FIG. 3) may be provided by a third-party provider (e.g., a hosted server or online database service).

Although the present embodiments have been illustrated principally in relation to ultrasound scanning, they may have application in respect of other scenarios in which a remote reviewer is reviewing, in real time, a live process that an operator is performing.

In the discussion above, the present embodiments have generally been described in the context of a reviewer assisting with a live medical examination by an operator. However, in various embodiments, the present embodiments may also be used in an educational setting. For example, in these instances, the operator 202 may be a student learning ultrasound techniques and the reviewer 276 may be an instructor providing live feedback and/or instruction on scanning technique. In these embodiments, the live reviewer list may be selected based on available education courses made available by an instructor reviewer, and the operator may join the virtual room 340 at a prescheduled time for an instructional session on ultrasound scanning.

As noted above with respect to FIG. 4, in some embodiments, there may be data transmitted by the data module 440 to the computing device 274 via data links 442, 444. In environments where embodiments are being used in education settings, this data may include information about the student (e.g., whether they're a student, resident, staff, and/or their medical specialty), the education history of a student learning ultrasound (e.g., the number of courses they have taken, their attendance record at the online learning sessions, or the like). In various embodiments, the scanner 204 may be provided with a gyroscope, altimeter, and/or accelerometer, such that signals from these sensors may be transmitted in the tele-ultrasound session to the reviewer computing device 274 so as to allow them to see the movement and/or position of the scanner 204. For example, the display of such scanner data 204 at the reviewer computing device 274 may involve a 3D model of the scanner 204, and the 3D model may move in 3D space on the display of the reviewer 276 based on this sensor data received from the scanner 204.

As discussed above in relation to FIG. 5, an online administration portal may allow for addition or removal of certain users within an institution to the live reviewer list retrieved at act 520. In the education context, the live reviewers may be ultrasound experts, instructors or educators who are running courses to teach students how to use ultrasound. In such embodiments, the online administration portal may be configured to facilitate addition of reviewers who are course instructors. For example, additional or alternative to an administrator portal that allows addition or removal of live reviewers to the live reviewer list, the online portal may provide a course instructor role and/or be a separate dedicated online course instructor portal. Such a portal may provide software functionality to assist live reviewers organize their courses. For example, this functionality may include the ability for course instructors to add their availability in a calendar and/or schedule for when course instruction via a tele-ultrasound session is available. In various embodiments, this calendar/schedule may be referred to when the live reviewer list is retrieved at act 520 in FIG. 5.

Additionally or alternatively, the portal may allow for an instructor to upload course descriptions, an instructor profile, instructor qualifications, ultrasound equipment they're familiar with, medical specialties teachable by the instructor, and/or assets or other media that may help a student learn ultrasound (e.g., videos or models usable in an AR session by a student).

In various embodiments, the portal may connect to a course marketplace that shows the various information that can be uploaded by a course instructor (including schedule, and course descriptions). This course marketplace may then be accessed by students who desire to learn ultrasound to book tele-ultrasound instruction sessions that make use of the various embodiments described herein.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, support assembly, valve device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and subcombinations as may reasonably be inferred. The scope of the claims should not be limited by the embodiments set forth in the examples but should be given the broadest interpretation consistent with the description as a whole.

D. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

To aid the Patent Office and any readers of any patent issued on this applications in interpreting the claims appended hereto, applicant wishes to note that they do not intend any of the appended claims or claim elements to invoke 35 U.S.C. 112(f) unless the words "means for" or "step for" are explicitly used in the particular claim.

E. Claim Support

In a first broad aspect of the present disclosure, there is provided a method for automatically establishing a communication session for live review of ultrasound scanning including the steps of: displaying, by an application running on a mobile device, an ultrasound image obtained by a scanner connected to the mobile device; detecting, by the application, a trigger; in response to the trigger, sending, by the application, a request for review to a server; receiving, by the application, connection information from the server for connecting to a virtual room; connecting, by the application, the mobile device to the virtual room using the connection information; transmitting, by the application, the ultrasound image to the virtual room; and outputting, by the application, audio signals received from a responding computing device, wherein the responding computing device is connected to the virtual room.

In some embodiments, the application connects to the virtual room without requiring input after detecting the trigger. In some embodiments, the trigger is a single tap on a button displayed by the application on the mobile device. In some embodiments, the connection information includes login credentials to the virtual room.

In some embodiments, the responding computing device is one of a plurality of available responding computing devices; and after the sending, by the application, of the request for review to the server, the method further includes: sending, from the server, in response to the request, a notification to each of the plurality of available responding computing devices; and connecting the responding computing device of the plurality of available responding computing devices to the virtual room.

In some embodiments, the method further includes receiving a response to the notification at the responding computing device, wherein the responding computing device connects to the virtual room without requiring input of connection information after receipt of the response to said notification.

In some embodiments, the connection information for connecting the responding computing device to the virtual room is included in the notification sent to the responding computing device.

In some embodiments, the method further includes: capturing, by a camera of the mobile device, a live video of the scanner connected to the mobile device; and merging a video stream of the camera with a video stream of the ultrasound image; wherein transmitting the ultrasound image to the virtual room is achieved by transmitting the merged video streams to the virtual room.

In some embodiments, the method further includes: receiving, by the responding computing device, the merged video streams; and displaying, concurrently on the responding computing device, the ultrasound image and the live video of the scanner connected to the mobile device.

In some embodiments, the method further includes establishing a two-way audio connection between the mobile device and the responding computing device.

In some embodiments, the method further includes: capturing, by a supplementary camera connected to the mobile device, a live video of a scanner connected to the mobile device; and merging a video stream of the supplementary camera with a video stream of the ultrasound image; wherein transmitting the ultrasound image to the virtual room is achieved by transmitting the merged video streams to the virtual room.

In some embodiments, the method further includes: displaying a live video image from the responding computing device on the mobile device; and displaying a live video image from the mobile device on the responding computing device.

In some embodiments, the connection information is received by the application before the application is initialized.

In some embodiments, the method further includes: receiving, by the application, from the responding computing device, coordinates of a point on the ultrasound image; and displaying, by the application, a cursor on the ultrasound image displayed on the mobile device, at the coordinates.

In some embodiments, the trigger is said displaying of the ultrasound image.

In another broad aspect of the present disclosure, there is provided a system for automatically establishing a communication session for live review of ultrasound scanning including: a server; an ultrasound scanner; a mobile device connected to the server and ultrasound scanner; and a responding computing device connected to the server; wherein the mobile device runs an application that is configured to: display an ultrasound image obtained by the scanner; detect a trigger; in response to the trigger, send a request for review to the server; receive connection information from the server for connecting to a virtual room; connect the mobile device to the virtual room using the connection information; transmit the ultrasound image to the virtual room; and output audio signals received from the responding computing device; and wherein the responding computing device is connected to the virtual room.

In some embodiments, the application connects to the virtual room without requiring input to the mobile device after detecting the trigger; the trigger is a one-click input on the mobile device; the connection information includes login credentials to the virtual room; the responding computing device is one of a plurality of available responding computing devices; after sending the request for review to the server, the server is configured to send, in response to the request, a notification to each of the plurality of responding computing devices; the responding computing device is configured to connect to the virtual room without requiring input of connection information after receiving a response to said notification at the responding computing device; and the mobile device is connected to the responding computing device via: a one-way video link from the mobile device to the responding computing device, which carries the ultrasound image and a video captured by a camera of the mobile device; and a two-way audio link that permits audio interaction between the mobile device and the responding computing device.

In some embodiments, the system includes a supplementary camera connected to the mobile device, wherein the application is configured to: merge a video stream of the supplementary camera with a video stream of the ultrasound image; and transmit the ultrasound image to the virtual room by transmitting the merged video streams to the virtual room.

In some embodiments, the server includes a main server, a push notification server and a web real-time communication server, wherein: the main server is configured to: obtain the connection information from a database; receive the request for review; and transmit a notification request to a push notification server; the push notification server is configured to: receive the notification request; and transmit a notification to the responding computing device; and the web real-time communication server is configured to provide the virtual room.

In another broad aspect of the present disclosure, there is provided non-transitory computer readable media for automatically establishing a communication session for live review of ultrasound scanning, the media includes computer-readable instructions, which, when executed by one or more processors cause an application running on a mobile device to: display an ultrasound image obtained by a scanner connected to the mobile device; detect a trigger; in response to the trigger, send a request for review to a server; receive connection information from the server for connecting to a virtual room; connect the mobile device to the virtual room using the connection information; transmit the ultrasound image to the virtual room; and output audio signals received from a responding computing device, wherein the responding computing device is connected to the virtual room.

The invention claimed is:

1. A method for establishing a communication session for live review of ultrasound scanning, the method:
a mobile device displaying an ultrasound image obtained by a scanner connected to the mobile device;
the mobile device receiving a single input to initiate the communication session for live review of the ultrasound image obtained by the scanner connected to the mobile device;
in response to receipt of the single input, the mobile device sending a request for review to a server;
the mobile device receiving connection information from the server for connecting to a virtual room, the connection information comprising a virtual room identifier and a network location that allows for entrance into the virtual room by any computing device, the mobile device not having connection information for the virtual room prior to receipt of the single input;
the server retrieving a list of live responding reviewers and sending, in response to the request, a notification to each of a plurality of responding computing devices, the notification comprising the connection information for the virtual room for the plurality of responding computing devices to connect to the virtual room;
the mobile device connecting to the virtual room using the connection information for the virtual room;
a responding computing device, of the plurality of responding computing devices, connecting to the virtual room using the connection information for the virtual room without requiring further input of connection information after receipt of an input responding to the notification at the responding computing device;
upon the responding computing device using the connection information to also connect to the virtual room, the mobile device connecting to the responding computing device via the virtual room;
the mobile device transmitting the ultrasound image to the virtual room, and the ultrasound image is provided to the responding computing device via the virtual room; and
the mobile device outputting audio signals received, via the virtual room, from the responding computing device.

2. The method of claim 1, wherein the mobile device connects to the virtual room without requiring further input after receipt of the single input.

3. The method of claim 1, wherein the single input is a single tap on a button displayed by an application on the mobile device.

4. The method of claim 1, wherein the connection information for connecting to the virtual room further comprises login credentials to the virtual room.

5. The method of claim 1, further comprising:
capturing, by a camera of the mobile device, a live video of the scanner connected to the mobile device; and
merging a video stream of the camera with a video stream of the ultrasound image;
wherein transmitting the ultrasound image to the virtual room is achieved by transmitting the merged video streams to the virtual room.

6. The method of claim 5, further comprising:
receiving, at the responding computing device, the merged video streams; and
displaying, concurrently on the responding computing device, the ultrasound image and the live video of the scanner connected to the mobile device.

7. The method of claim 1, further comprising establishing a two-way audio connection between the mobile device and the responding computing device.

8. The method of claim 1, further comprising:
capturing, by a supplementary camera connected to the mobile device, a live video of a scanner connected to the mobile device; and
merging a video stream of the supplementary camera with a video stream of the ultrasound image;

wherein transmitting the ultrasound image to the virtual room is achieved by transmitting the merged video streams to the virtual room.

9. The method of claim 1, further comprising:
displaying a live video image from the responding computing device on the mobile device; and
displaying a live video image from the mobile device on the responding computing device.

10. The method of claim 1, wherein the connection information for connecting to the virtual room is also provided as configuration data that is provisioned at the mobile device before an application for displaying the ultrasound image obtained by the scanner is initialized at the mobile device.

11. The method of claim 1, further comprising:
receiving, at the mobile device, from the responding computing device, coordinates of a point on the ultrasound image; and
displaying a cursor on the ultrasound image displayed on the mobile device, at the coordinates.

12. A system for establishing a communication session for live review of ultrasound scanning, the system comprising:
a server;
an ultrasound scanner;
a mobile device connected to the server and ultrasound scanner; and
a responding computing device capable of being connected to the server;
wherein the mobile device is configured to:
display an ultrasound image obtained by the scanner;
receive a single input to initiate the communication session for live review of the ultrasound image obtained by the scanner connected to the mobile device;
in response to single input, send a request for review to the server, wherein the server retrieves a list of live responding reviewers and the server is configured to send, in response to the request, a notification to each of a plurality of responding computing devices, the notification comprising the connection information for the virtual room;
receive connection information from the server for connecting to a virtual room, the connection information comprising a virtual room identifier and a network location that allows for entrance into the virtual room by any computing device, the mobile device not having the connection information prior to receipt of the single input, wherein a responding computing device of the plurality of responding computing devices connects to the virtual room using the connection information for the virtual room without requiring further input of connection information after receipt of an input responding to the notification at the responding computing device;
connect the mobile device to the virtual room using the connection information for the virtual room;
upon the responding computing device using the connection information to also connect to the virtual room, connect the mobile device to the responding computing device via the virtual room;
transmit the ultrasound image to the virtual room, and the ultrasound image is provided to the responding computing device via the virtual room; and
output audio signals received, via the virtual room, from the responding computing device.

13. The system of claim 12, wherein:
the mobile device connects to the virtual room without requiring further input after receipt of the single input;
the single input is a one-click input on the mobile device;
the connection information for connecting to the virtual room further comprises login credentials to the virtual room;
wherein the connection between the mobile device and the responding computing device comprises:
a one-way video link from the mobile device to the responding computing device, which carries the ultrasound image and a video captured by a camera of the mobile device; and
a two-way audio link that permits audio interaction between the mobile device and the responding computing device.

14. The system of claim 12, comprising a supplementary camera connected to the mobile device, wherein the mobile device is configured to:
merge a video stream of the supplementary camera with a video stream of the ultrasound image; and
transmit the ultrasound image to the virtual room by transmitting the merged video streams to the virtual room.

15. The system of claim 12, wherein the server comprises a main server, a push notification server, and a web real-time communication server, wherein:
the main server is configured to:
obtain the connection information from a database;
receive the request for review; and
transmit a notification request to a push notification server;
the push notification server is configured to:
receive the notification request; and
transmit a notification to each of the plurality of responding computing devices, the notification comprising the connection information for the virtual room; and
the web real-time communication server is configured to provide the virtual room.

16. Non-transitory computer readable media for establishing a communication session for live review of ultrasound scanning, the media comprising computer-readable instructions, which, when executed by one or more processors on a mobile device, configures the mobile device to:
display an ultrasound image obtained by a scanner connected to the mobile device;
receive a single input to initiate the communication session for live review of the ultrasound image obtained by the scanner connected to the mobile device;
in response to receipt of the single input, send a request for review to a server, wherein the server retrieves a list of live responding reviewers and is configured to send, in response to the request, a notification to each of a plurality of responding computing devices, the notification comprising the connection information for the virtual room;
receive connection information from the server for connecting to a virtual room, the connection information comprising a virtual room identifier and a network location that allows for entrance into the virtual room by any computing device, the mobile device not having the connection information prior to receipt of the single input wherein a responding computing device of the plurality of responding computing devices connects to the virtual room using the connection information for the virtual room without requiring further input of connection information after receipt of an input responding to the notification at the responding computing device;

connect the mobile device to the virtual room using the connection information for the virtual room;

upon the responding computing device using the connection information to also connect to the virtual room, connect the mobile device to the responding computing device via the virtual room;

transmit the ultrasound image to the virtual room, and the ultrasound image is provided to the responding computing device via the virtual room; and output audio signals received, via the virtual room, from the responding computing device.

* * * * *